(12) United States Patent
Nemoto

(10) Patent No.: US 7,500,961 B2
(45) Date of Patent: Mar. 10, 2009

(54) CHEMICAL LIQUID INJECTION SYSTEM DETECTING MOUNT AND DISMOUNT OF CHEMICAL LIQUID SYRINGE TO AND FROM CHEMICAL LIQUID INJECTOR

(75) Inventor: Shigeru Nemoto, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 309 days.

(21) Appl. No.: 10/563,567

(22) PCT Filed: Jul. 6, 2004

(86) PCT No.: PCT/JP2004/009557

§ 371 (c)(1),
(2), (4) Date: Jan. 6, 2006

(87) PCT Pub. No.: WO2005/002650

PCT Pub. Date: Jan. 13, 2005

(65) Prior Publication Data

US 2006/0151049 A1 Jul. 13, 2006

(30) Foreign Application Priority Data

Jul. 7, 2003 (JP) ............................. 2003-193101

(51) Int. Cl.
*A61M 1/00* (2006.01)
(52) U.S. Cl. ..................................................... 604/151
(58) Field of Classification Search ................. 604/151; 600/432; 141/27, 94
See application file for complete search history.

(56) References Cited

U.S. PATENT DOCUMENTS 5,741,232 A * 4/1998 Reilly et al. ................. 604/154
2001/0021823 A1 * 9/2001 Nemoto ....................... 604/154

FOREIGN PATENT DOCUMENTS

| JP | 1984-228852 | 12/1984 |
| JP | 09-122234 | 5/1997 |
| JP | 2002-011096 | 1/2002 |
| JP | 2003-070911 | 3/2003 |
| JP | 2003-297175 | 10/2003 |

OTHER PUBLICATIONS

Archibold, Randal C. "Hospital Details Failures Leading to M.R.I. Fatality." Aug. 22, 2001, The New York Times.*

* cited by examiner

*Primary Examiner*—Nicholas D Lucchesi
*Assistant Examiner*—Victoria P Campbell
(74) *Attorney, Agent, or Firm*—Knobbe, Martens, Olson & Bear LLP

(57) ABSTRACT

The present invention includes mount-detecting means 131 placed at the position of liquid injector 100 where liquid syringe 200 is mounted and removed. This allows mount-detecting means 131 to detect the mount and dismount of liquid syringe 200 on and from liquid injector 100, and the detection result can be output to notify the operator, and/or the operation of piston actuating mechanism 116 can be controlled in accordance with the detection result. Thus, the present invention provides liquid injector 100 which can detect the mount and dismount of liquid syringe 200 on and from liquid injector 100.

14 Claims, 11 Drawing Sheets

CHEMICAL LIQUID INJECTION SYSTEM DETECTING MOUNT AND DISMOUNT OF CHEMICAL LIQUID SYRINGE TO AND FROM CHEMICAL LIQUID INJECTOR

RELATED APPLICATIONS

This application is the U.S. National Phase under 35 U.S.C. § 371 of International Application PCT/JP2004/009557, filed Jul. 6, 2004, which claims priority to Japanese Patent Application No. 2003-193101, filed on Jul. 7, 2003. The International Application was published under PCT Article 21(2) in a language other than English.

TECHNICAL FIELD

The present invention relates to a liquid injection system for injecting liquid into a patient by relatively moving a cylinder member and a piston member of a liquid syringe that is mounted on a liquid injector, and more particularly relates to a liquid injection system in which a liquid syringe is mounted on a liquid injector by a cylinder adapter.

BACKGROUND ART

Presently available imaging diagnostic apparatus for capturing fluoroscopic images of patients include CT (Computed Tomography) scanners, MRI (Magnetic Resonance Imaging) apparatus, PET (Positron Emission Tomography) apparatus, ultrasonic diagnostic apparatus, angiography apparatus, and MRA (MR Angiography) apparatus.

When such imaging diagnostic apparatus are used to capture a fluoroscopic image of a patient, it is occasionally practiced to inject a liquid such as a contrast media or a saline solution into the patient. A liquid injector for automatically injecting a liquid into a patient has been commercially available. Such a liquid injector has a main injector body on which a liquid syringe is removably mounted.

The liquid syringe has a hollow cylinder member filled with a liquid and a cylindrical piston member slidably inserted in the cylinder member. Generally, the cylinder member has an annular cylinder flange disposed on the outer circumferential edge of the rear end thereof, and the piston member has an annular piston flange disposed on the outer circumferential edge of the rear end thereof.

When the liquid injector is in use, the cylinder member of the liquid syringe which is filled with the liquid is connected to the patient by an extension tube, and the liquid syringe is mounted on the main injector body. In general liquid injectors, the main injector body has a concave defined in its upper surface complementary in shape to the cylinder member of the liquid syringe and its cylinder flange. Therefore, the liquid syringe is held on the main injector body when the cylinder member and the cylinder flange are placed in the concave.

The liquid injector also has a piston actuating mechanism for holding the piston flange independently of the cylinder member and sliding the piston member into and out of the cylinder member. When the piston member is pushed into the cylinder member, the liquid in the cylinder member can be injected into the patient. When the piston member is pulled out of the cylinder member, the cylinder member can draw the liquid from a liquid container.

Generally, in order to allow the liquid injector to hold various types of liquid syringes having various shapes, the concave defined in the upper surface of the main injector body is shaped to be able to receive the cylinder member of the liquid syringe having the maximum size. Liquid syringes having sizes other than the maximum size are combined with respective dedicated cylinder adapters and placed in the concave in the main injector body.

Cylinder adapters generally have concaves defined in their upper surfaces complementary in shape to the cylinder members of the liquid syringes and their cylinder flanges as the main injector body does. The cylinder members of the liquid syringes and their cylinder flanges are held in the concaves in the cylinder adapters. The cylinder adapters have lower surfaces whose outer profiles are similar to the outer profile of the cylinder member of the liquid syringe having the maximum size and the cylinder flange thereof, and are placed in the concave in the main injector body.

Liquid injectors constructed as described above have been invented by the inventor of the present invention and filed for patent (see, for example, Patent documents 1 and 2 shown below):

List of References

Patent document 1: Japanese laid-open patent publication No. 2002-11096.

Patent document 2: Japanese laid-open patent publication No. 2002-102343.

The above liquid injectors hold a liquid syringe when the cylinder member is directly placed in the concave in the main injector body or when the cylinder adapter with the cylinder member mounted in its concave is placed in the concave in the main injector body.

However, the liquid syringe may not be mounted suitably on the liquid injector, for example when the liquid syringe mounted on the liquid injector falls off during the injection operation. The operator needs to check appropriately the liquid syringe suitably mounted on the liquid injector to prevent the fall, which is difficult to achieve in reality.

DISCLOSURE OF INVENTION

The present invention has been made in view of the above-mentioned problem, and it is an object thereof to provide a liquid injection system which can detect mount and dismount (i.e. attachment and detachment) of a liquid syringe on and from a liquid injector.

The liquid injection system according to the present invention includes a liquid syringe and a liquid injector. The liquid syringe has a cylinder member and a piston member which is slidably inserted into the cylinder member. The cylinder member is filled with a liquid in advance. The liquid injector includes a cylinder holding mechanism, a piston actuating mechanism, and a mount-detecting means.

The cylinder holding mechanism receives the cylinder member of the liquid syringe mounted removably thereon. The piston actuating mechanism relatively moves the piston member with respect to the cylinder member of the liquid syringe. The mount-detecting means detects contact and separation of the cylinder member when it is mounted on and removed from the cylinder holding mechanism, respectively.

Thus, in the liquid injection system of the present invention, the liquid injector can detect the mount and dismount of the liquid syringe, so that the detection result can be output to notify the operator, or the operation of the piston actuating mechanism can be controlled in accordance with the detection result, for example.

Various means referred to in the present invention may be arranged to perform their functions, and may comprise dedicated hardware for performing a predetermined function, a data processing apparatus whose predetermined function is given by a computer program, a predetermined function performed by a data processing apparatus according to a computer program, or a combination thereof.

Various components referred to in the present invention do not need to be a separate entity. Rather, these components may be constructed as one component, a certain component may be part of another component, or a certain component may have a portion overlapping a portion of another component.

Certain terms with respect to forward, rearward, upward, downward, leftward, and rightward directions which will be referred to in the description are used for convenience only to simplify the illustration of relative positional relationships of various parts, and should not be interpreted as being limited to directions that are involved when the liquid injection system is manufactured and used.

BEST MODE FOR CARRYING OUT THE INVENTION

Configuration of Embodiment

Figure 1:
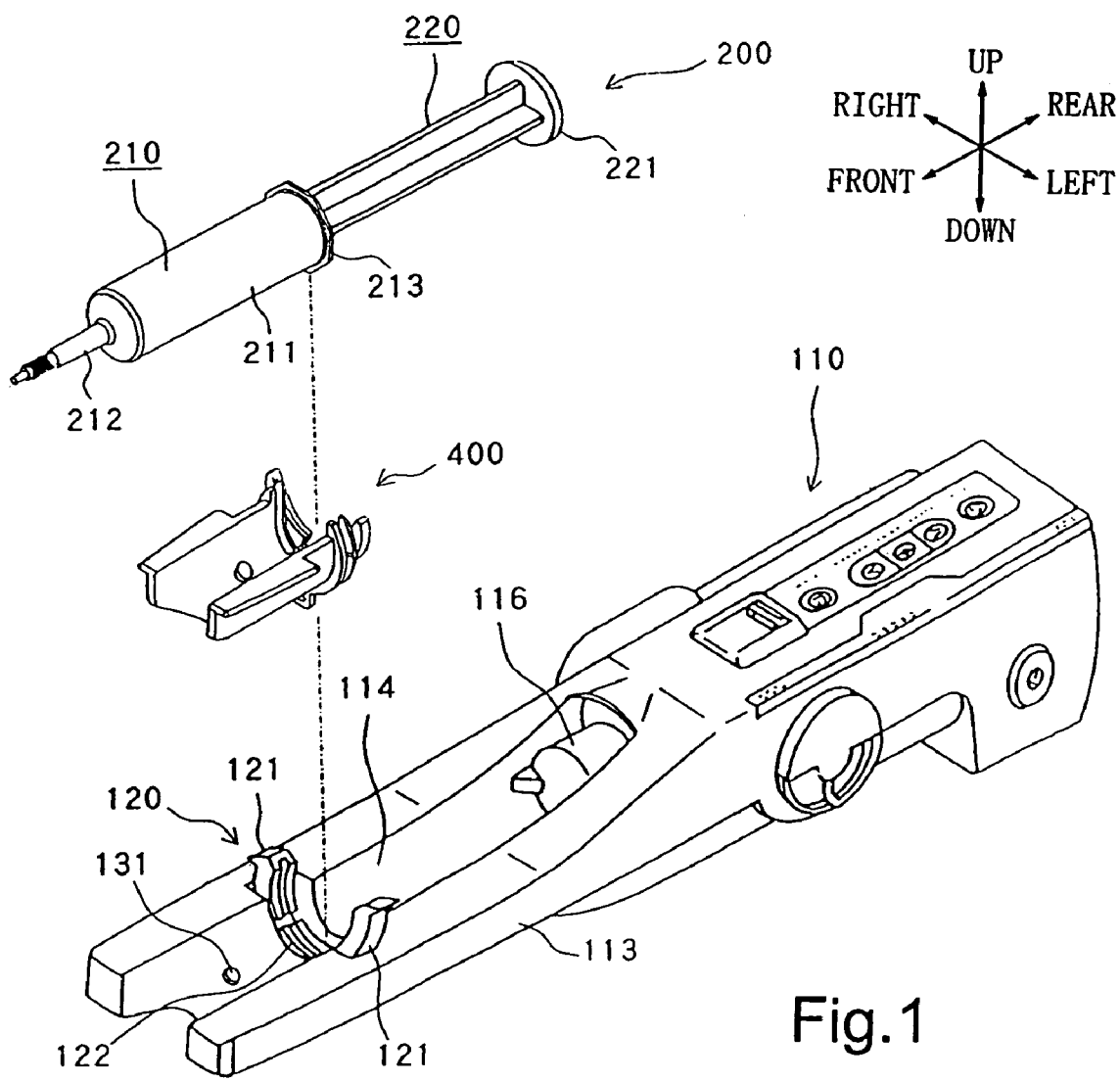
FIG. 1 is a perspective view showing the manner in which a liquid syringe is mounted on a liquid injector by a cylinder adapter of a liquid injection system according to the present invention.
Figure 2:
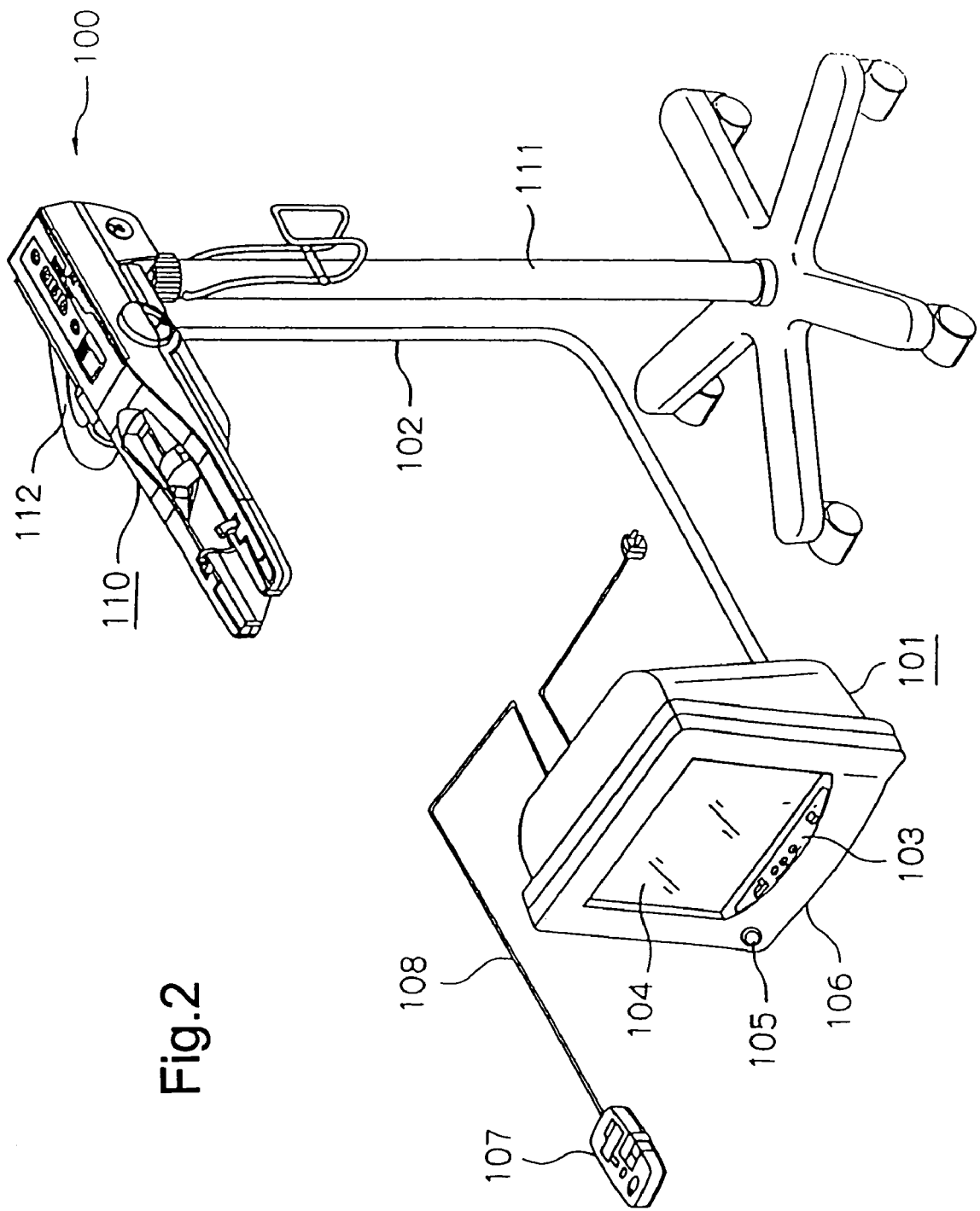
FIG. 2 is a perspective view showing an exterior appearance of the liquid injector.
Figure 3:
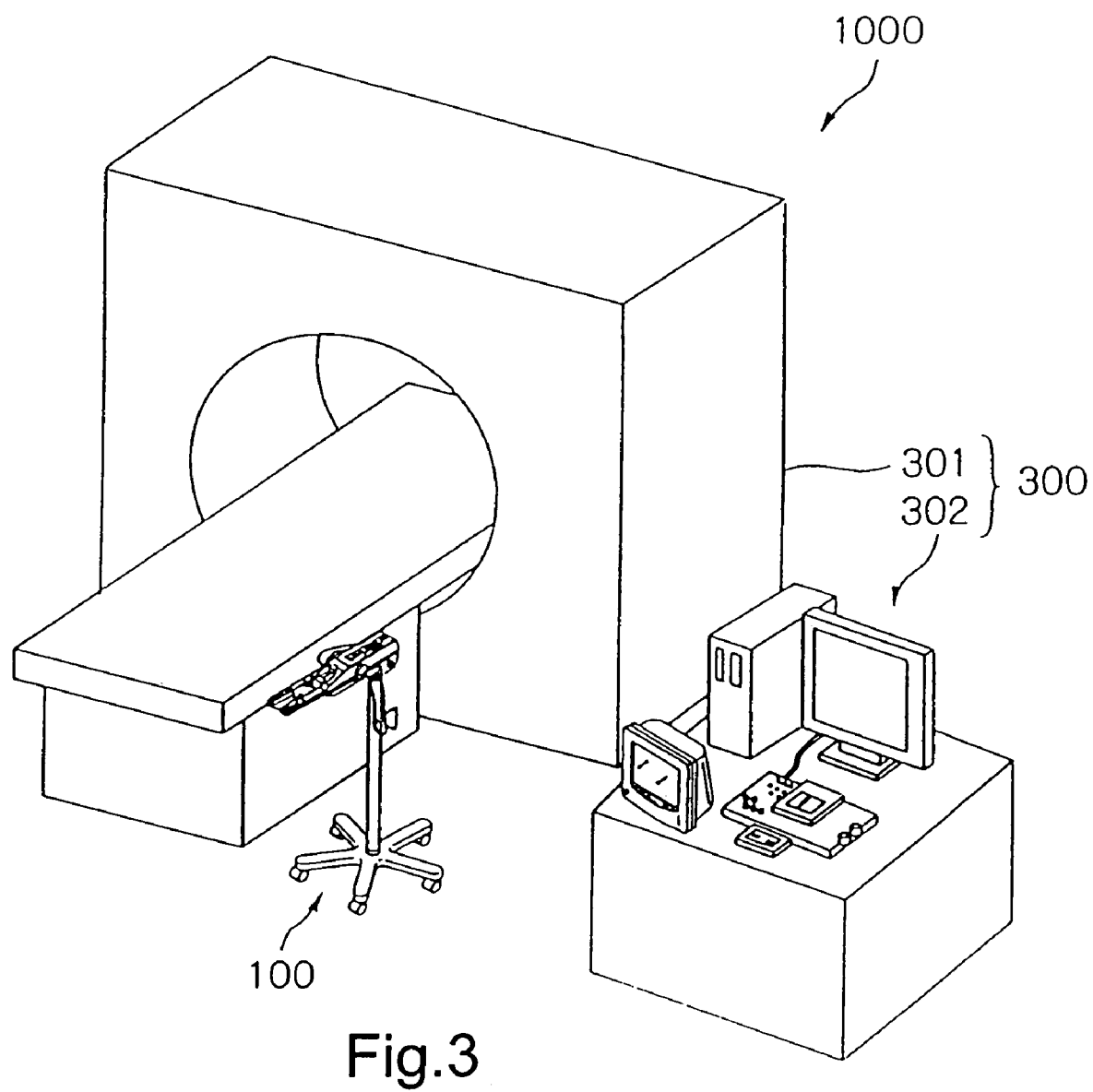
FIG. 3 is a perspective view showing an exterior appearance of the liquid injection system.
Figure 4A:
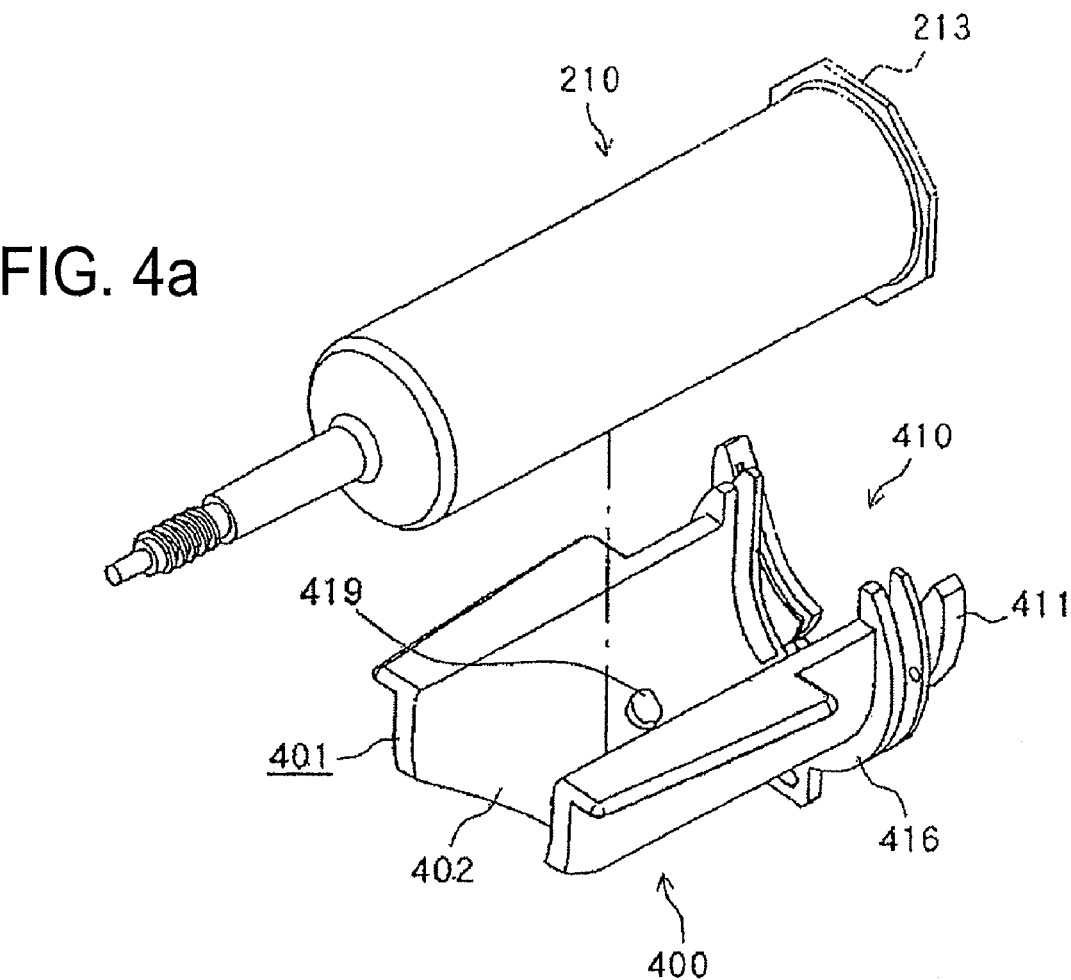
FIGS. 4a and 4b are perspective views showing the manner in which a liquid syringe is mounted on a cylinder adapter.
Figure 4B:
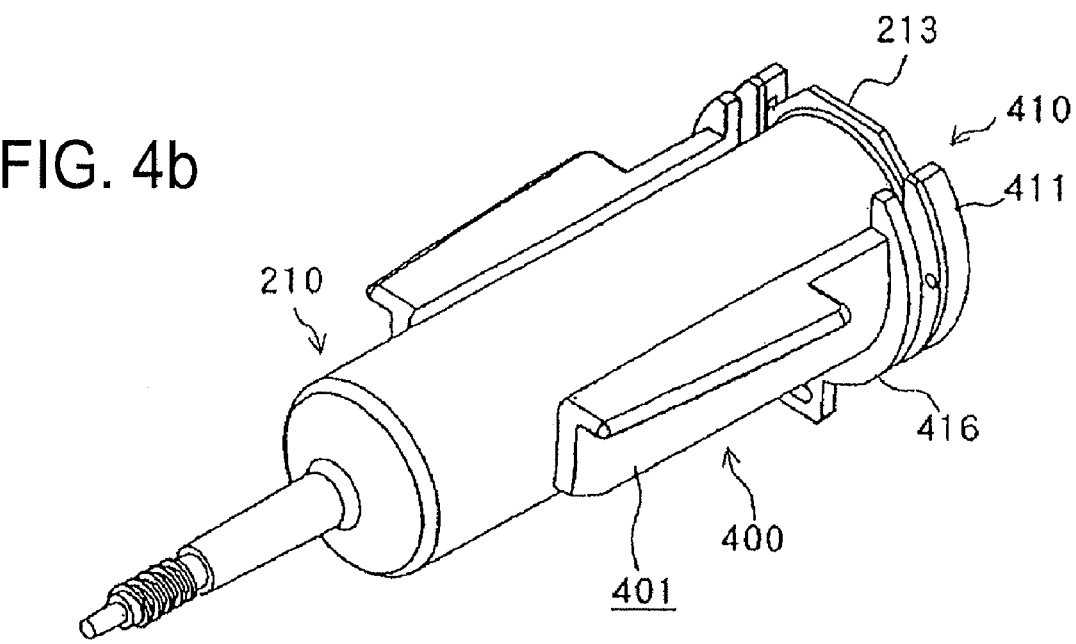
Figure 5A:
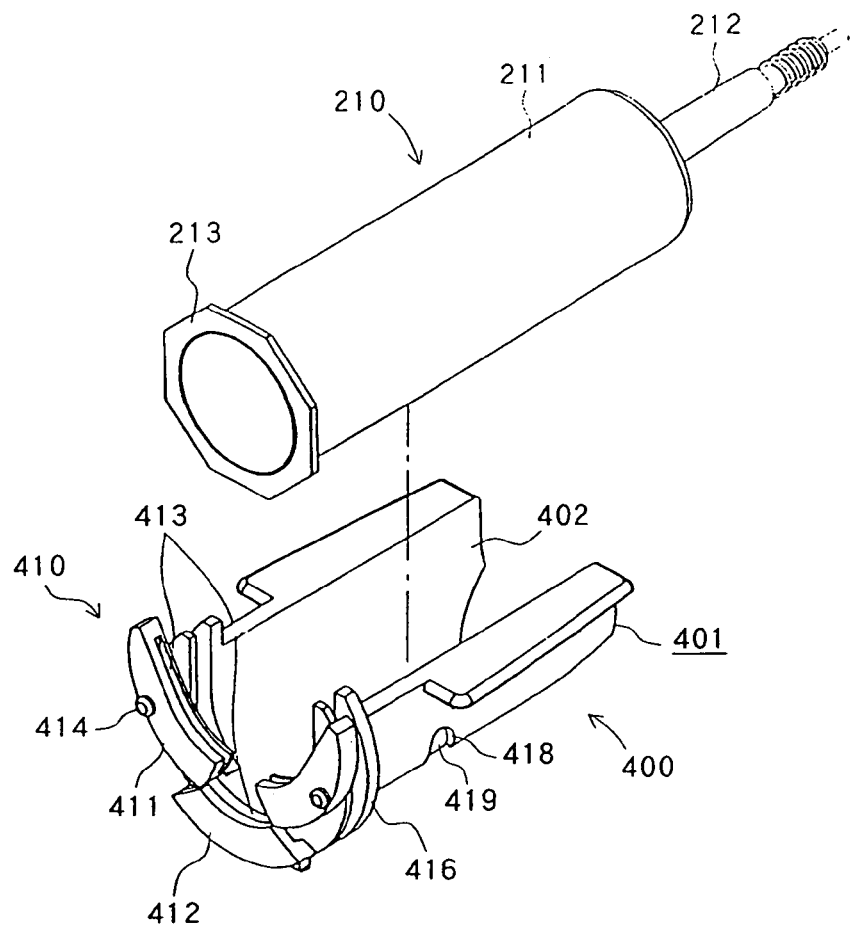
FIGS. 5a and 5b are perspective views showing the manner in which a liquid syringe is mounted on a cylinder adapter.
Figure 5B:
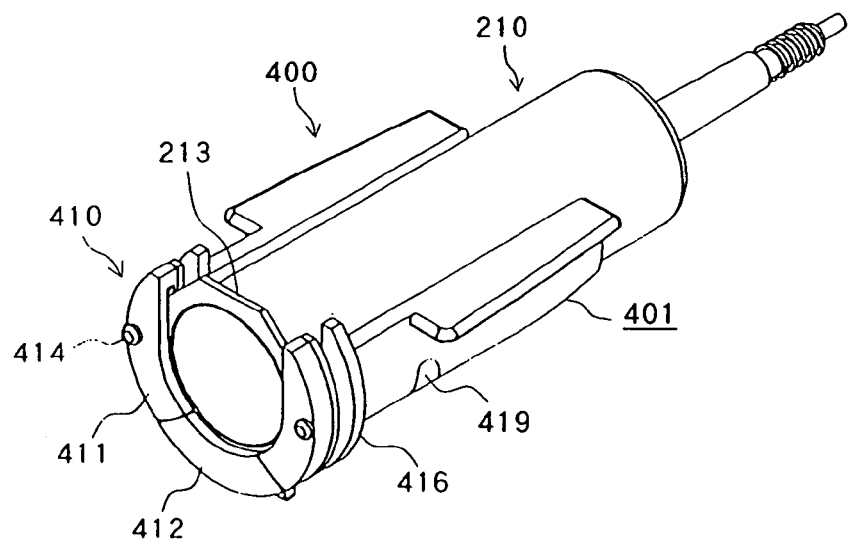

As shown in FIGS. 1 to 3, liquid injection system 1000 according to the present invention has liquid injector 100, liquid syringe 200, MRI apparatus 300 as an imaging diagnostic apparatus, and cylinder adapter 400. When a fluoroscopic image of a patient (not shown) is to be captured by MRI apparatus 300, liquid injector 100 injects a liquid such as a contrast media or a saline solution from liquid syringe 200 into the patient.

As shown in FIG. 3, MRI apparatus 300 comprises imaging unit 301 as an image capturing mechanism and control unit 302 which are connected to each other by a wired communication network (not shown). Imaging unit 301 captures a tomographic image of the patient, and control unit 302 controls operation of imaging unit 301.

As shown in FIG. 1, liquid syringe 200 comprises cylinder member 210 and piston member 220 slidably inserted in cylinder member 210. Cylinder member 210 has hollow cylindrical cylinder casing 211 with conduit 212 disposed on a closed distal end thereof.

Cylinder casing 211 of cylinder member 210 has an open end remote from the closed distal end thereof, and piston member 220 is inserted into cylinder casing 211 through the open end. Cylinder casing 211 has cylinder flange 213 disposed on the outer circumferential edge of the open end thereof. Piston member 220 has piston flange 221 disposed on the outer circumferential edge of an end thereof.

As shown in FIG. 2, liquid injector 100 comprises injection control unit 101 and injection head 110 as a main injector body which are separate from each other. Injection control unit 101 and injection head 110 are connected to each other by communication cable 102.

Injection head 110 actuates liquid syringe 200 mounted thereon to inject a liquid therefrom into the patient. Injection control unit 101 controls the operation of injection head 110. Injection control unit 101 houses a microcomputer 130 therein, and is connected to control unit 302 of MRI apparatus 300 by the wired communication network 312.

As shown in FIG. 2, injection control unit 101 has console panel 103, touch panel 104 as a display panel, and speaker unit 105 which are disposed on the front face of a unit housing 106. Separate controller unit 107 is connected to injection control unit 101 by connector 108.

Injection head 110 is mounted on the upper end of caster stand 111 by movable arm 112. As shown in FIG. 1, injection head 110 includes head body 113 as a cylinder holding structure having semi-cylindrical groove-like concave 114 defined in an upper surface thereof for receiving liquid syringe 200 removably mounted therein.

Injection head 110 has piston actuating mechanism 116 positioned rearwardly of concave 114 for holding and sliding piston flange 221, and flange holding mechanism 120 disposed forwardly of concave 114 for removably holding cylinder flange 213 of liquid syringe 200.

Piston actuating mechanism 116 has an ultrasonic motor (not shown) as a drive source which does not produce a magnetic field. The ultrasonic motor is made of a nonmagnetic material such as phosphor bronze alloy (Cu+Sn+P), titanium alloy (Ti–6Al–4V), magnesium alloy (Mg+Al+Zn), or the like.

Liquid injection system 1000 has liquid syringes 200 available for use in various different sizes. Only liquid syringe 200 having the maximum size is directly mounted in concave 114 in injection head 110, and other liquid syringes 200 having sizes other than the maximum size are selectively mounted in concave 114 with respective dedicated cylinder adapters 400.

Flange holding mechanism 120 of liquid injector 100 is of a structure for holding cylinder flange 213 of a liquid syringe having the maximum size. Cylinder adapter 400 has an outer profile which is of the same shape as liquid syringe 200 having the maximum size so that cylinder adapter 400 can be held by concave 114 and flange holding mechanism 120 of injection head 110.

Flange holding mechanism 120 has a pair of laterally spaced movable holders 121 and a single stationary holder 122 disposed between movable holders 121. Movable holders 121 and stationary holder 122 are disposed in an annular pattern. Stationary holder 122 has a semi-arcuate shape which is upwardly concave, and movable holders 121, each of a quarter arcuate shape, are disposed one on each side of stationary holder 122.

Movable and stationary holders 121, 122 have respective grooves defined in inner concave edges thereof. Cylinder flange 213 of liquid syringe 200 having the maximum size engages removably in the grooves in movable and stationary holders 121, 122. Movable holders 121 are pivotally supported by respective holder pivot support mechanisms (not shown) for vertical angular movement between an open position in which movable holders 121 are open upwardly for allowing cylinder flange 213 to be inserted into the grooves in movable and stationary holders 121, 122, and a closed position in which cylinder flange 213 is retained at its opposite sides in the grooves in movable and stationary holders 121, 122.

When movable holders 121 are in the closed position, their lower ends are positioned downwardly of the axes of the holder pivot support mechanisms and their upper ends are positioned upwardly of the axes of the holder pivot support mechanisms. Movable holders 121 are constructed as components separate from head body 113. However, movable holders 121 may be integrally formed with head body 113.

Figure 7A:
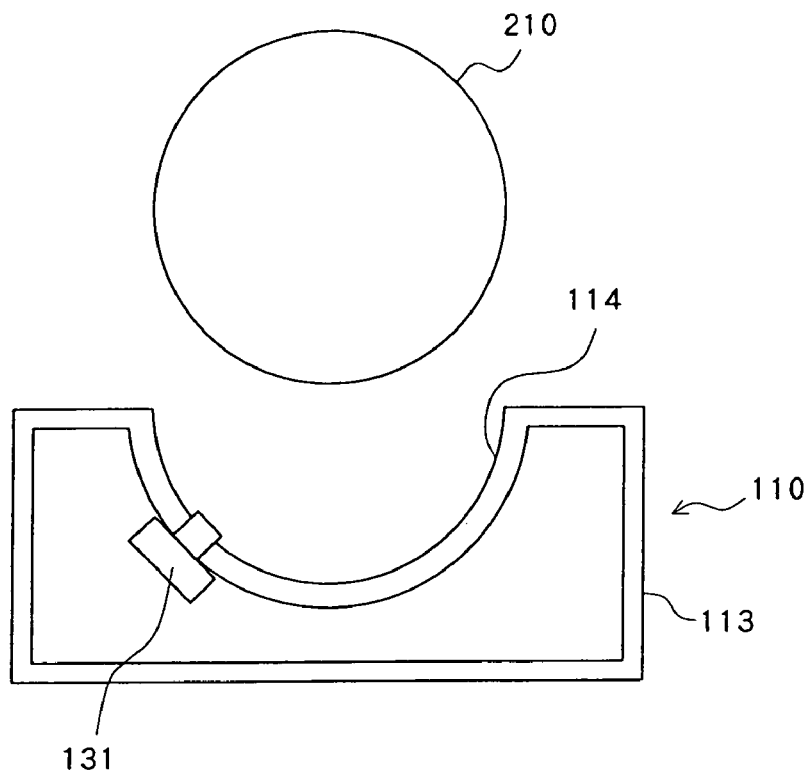
FIGS. 7a and 7b are vertical cross-sectional views showing the manner in which a liquid syringe is direct mounted on an injection head of a liquid injector.
Figure 7B:
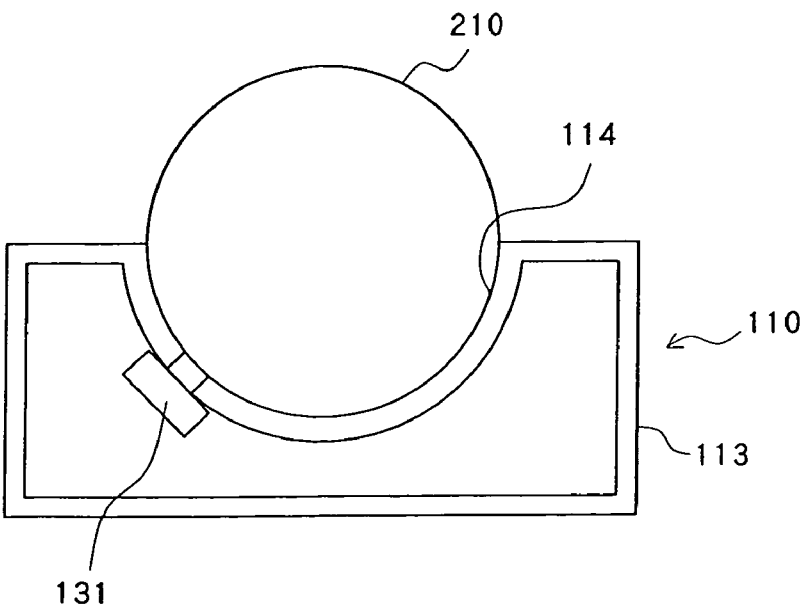

Injection head 110 has press switch 131 as a mount-detecting means near the bottom of concave 114. As shown in FIGS. 7a and 7b, press switch 131 detects cylinder member 210 having the maximum size installed in concave 114 when liquid syringe cylinder member 210 comes into contact with switch 131.

Figure 6:
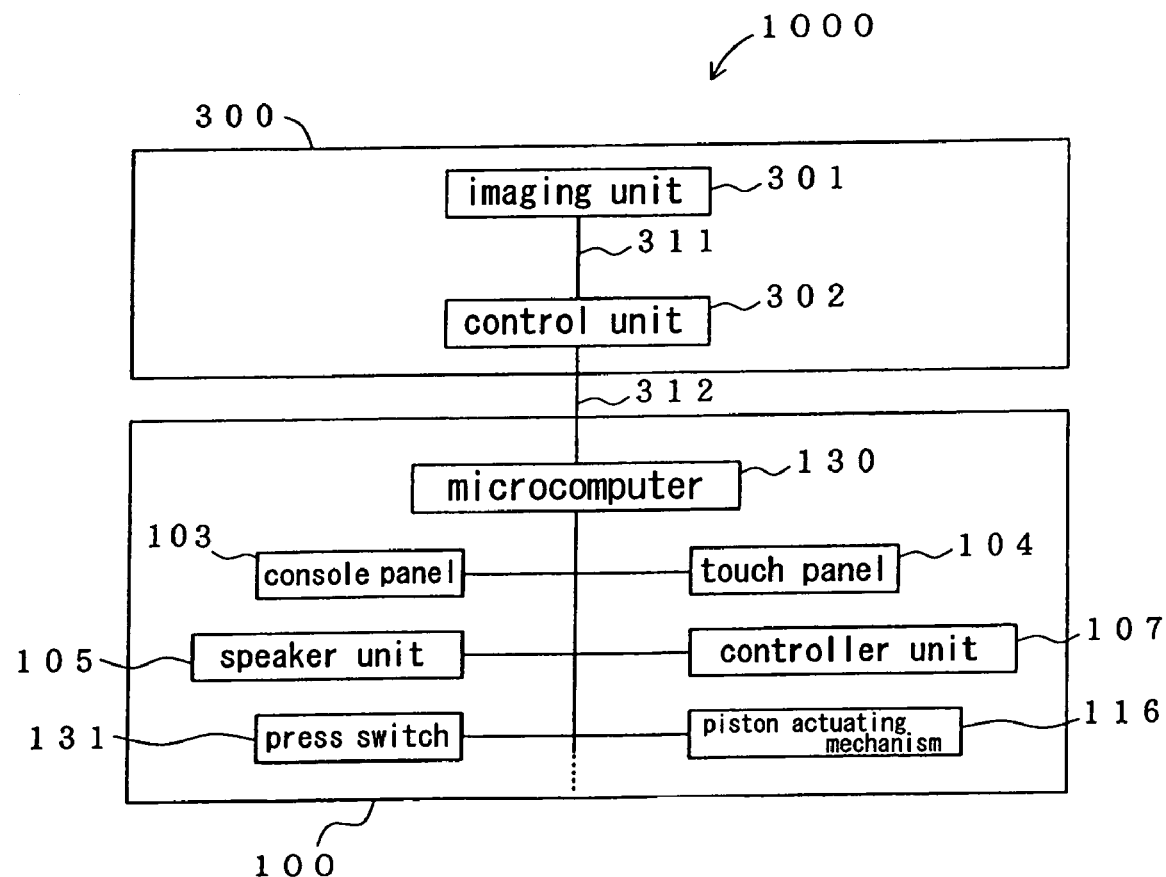
FIG. 6 is a block diagram illustrating the circuitry of the liquid injection system.

As shown in FIG. 6, the respective components of liquid injector 100 are connected to microcomputer 130 which controls the respective components according to a computer program installed therein. In a similar way, control unit 302 of MRI apparatus 300 is formed of a computer unit which controls the operation of imaging unit 301 according to a computer program installed therein.

In imaging diagnostic system 1000 of the embodiment, microcomputer 130 of liquid injector 100 and control unit 302 of MRI apparatus 300 communicate various types of data with each other to control coordination of various operations thereof. Thus, microcomputer 130 of liquid injector 100 serves as various means such as an actuating control means, and control unit 302 of MRI apparatus 300 serves as various means such as an imaging control means.

More specifically, microcomputer 130 of liquid injector 100 detects the mount and dismount of liquid syringe 200 on and from injection head 110 by press switch 131 and outputs the detection result as display on touch panel 104. Microcomputer 130 enables the operation of piston actuating mechanism 116 while it detects the mount of liquid syringe 200 on injection head 110, and it disables the operation thereof while it does not detect the mount.

Microcomputer 130 of liquid injector 100 transmits the abovementioned detection result of the mount or removal of liquid syringe 200 to control unit 302 of MRI apparatus 300. In response to that, control unit 302 enables the operation of imaging unit 301 when it receives the detection result indicating that liquid syringe 200 is mounted, and it disables the operation thereof when it receives the detection result indicating that liquid syringe 200 is not mounted.

The various means of liquid injector 100 and MRI apparatus 300 as described above are realized by using hardware such as touch panel 104 as required. However, the main part is realized by microcomputer 130 and imaging unit 302 performing various operations according to the computer programs installed therein.

Cylinder adapter 400 is prepared for each of liquid syringes 200 having sizes other than the maximum size. As shown in FIGS. 4a, 4b, 5a, and 5b, cylinder adapter 400 has adapter body 401 curved in U-shape. Adapter body 400 has concave 402 defined in an upper surface thereof and having a U-shaped cross-section for receiving cylinder member 210 of liquid syringe 200 removably mounted therein from above.

Cylinder adapter 400 has flange holding mechanism 410 positioned rearwardly of concave 402 for holding cylinder flange 213.

Flange holding mechanism 410 of cylinder adapter 400 has the similar structure to that of flange holding mechanism 120 of liquid injector 100, and has a pair of laterally spaced movable holders 411 and a single stationary holder 412. Movable and stationary holders 411 and 412 have concave grooves 413 defined in inner surfaces thereof. Cylinder flange 213 of liquid syringe 200 removably engages in concave grooves 413.

Movable holders 411 are pivotally supported by respective holder pivot support mechanisms 414 for vertical angular movement between an open position in which movable holders 411 are open upwardly for allowing cylinder flange 213 to be inserted into concave grooves 413 in movable and stationary holders 411, 412, and a closed position in which cylinder flange 213 is retained at its opposite sides in concave grooves 413 in movable and stationary holders 411, 412.

When movable holders 411 are in the closed position, their lower ends are positioned downwardly of the axes of holder pivot support mechanisms 414 and their upper ends are positioned upwardly of the axes of holder pivot support mechanisms 414. Stationary holder 412 is formed integrally with adapter body 401. However, stationary holder 412 may be constructed as a component separate from adapter body 401.

Adapter body 401 has a lower surface whose outer profile is of the same shape as cylinder member 210 of liquid syringe 200 having the maximum size, and has adapter flange 416 forwardly of flange holding mechanism 120 in its lower surface. The outer profile of adapter flange 416 is of the same shape as cylinder flange 213 of liquid syringe 200 having the maximum size.

As shown in FIGS. 4a, 4b, 5a, and 5b, movable holders 411 of cylinder adapter 400 protrude outward when they are placed in the open position. Thus, cylinder adapter 400 with its movable holders 411 in the closed position is mounted in concave 114 of liquid injector 100, but cylinder adapter 400 with its movable holders 411 in the open position is not mounted in concave 114.

Cylinder adapter 400 has throughhole 418 formed near the bottom of concave 402 and contact-transfer member 419 supported movably in throughhole 418. More specifically, as shown in FIGS. 8a, 8b, 9a, and 9b, throughhole 418 of cylinder adapter 400 is formed at the position corresponding to press switch 131 of injection head 110. Contact-transfer member 419 is biased to protrude into concave 402 from throughhole 418 by a bias mechanism (not shown) such as a plate spring.

When the adapter body with no cylinder member 210 mounted thereon is installed in head body 113, contact-transfer member 419 is biased to the position where it is not in contact with press switch 131. When the adapter body with cylinder member 210 mounted thereon is installed in head body 113, contact-transfer member 419 is moved to the position where it is in contact with press switch 131.

Adapter body 401 and movable holders 411 are made of engineering plastic or the like, and holder pivot support mechanisms 414 are made of a nonmagnetic material such as phosphor bronze alloy (Cu+Sn+P), titanium alloy (Ti–6Al–4V), magnesium alloy (Mg+Al+Zn), or the like. Therefore, cylinder adapter 400 is made of nonmagnetic materials.

Operation of Embodiment

The liquid injection system 1000 according to the present invention operates as follows: The operator selects liquid syringe 200 that is suitable for a liquid that is to be injected into the patient, and connects conduit 212 of selected liquid syringe 200 to the patient with an extension tube (not shown).

If selected liquid syringe 200 is of the maximum size which does not require the use of cylinder adapter 400, then cylinder member 210 thereof is directly placed in concave 114 in injection head 110, and cylinder flange 213 is held by flange holding mechanism 120 and piston member 220 is simultaneously gripped by cylinder actuating mechanism 116.

In that case, when liquid syringe 200 is inserted from above into concave 114 of injection head 110, movable holders 121 placed in the open position are automatically turned into the close position. Cylinder flange 213 is retained at its opposite sides in movable holders 121 and at its lower portion in stationary holder 122.

As shown in FIG. 7b, at this point, cylinder member 210 comes into contact with press switch 131 protruding into concave 114 of injection head 110, so that press switch 131 detects the mount of liquid syringe 200 on injection head 110.

If selected liquid syringe 200 is of a size other than the maximum size, then, as shown in FIG. 8, liquid syringe 200 is mounted on cylinder adapter 400, and then placed together with cylinder adapter 400 on injection head 110.

More specifically, if movable holders 411 of cylinder adapter 400 are in the open position, then when cylinder member 210 of liquid cylinder 200 is inserted from above into concave 402 to insert cylinder flange 213 into grooves 413, movable holders 411 are automatically turned into the closed position by being pressed by cylinder member 210.

Cylinder flange 213 of liquid syringe 200 is now retained at its opposite sides by movable holders 411 of cylinder adapter 400, and retained at its lower side by stationary holder 412.

Figure 8A:
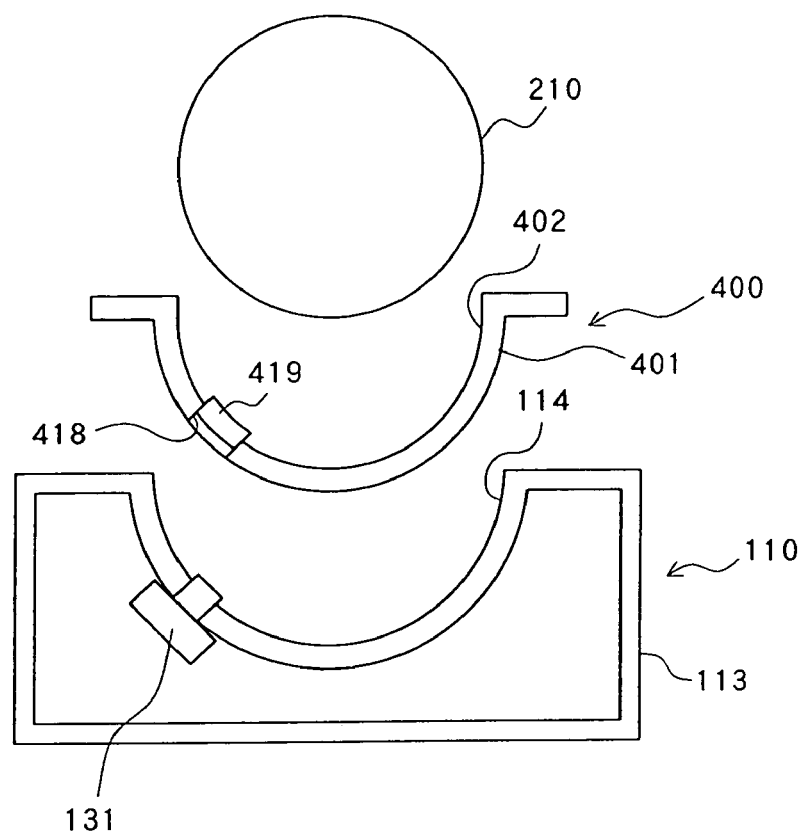
FIGS. 8a and 8b are vertical cross-sectional views showing the manner in which a liquid syringe is mounted on a cylinder adapter.
Figure 8B:
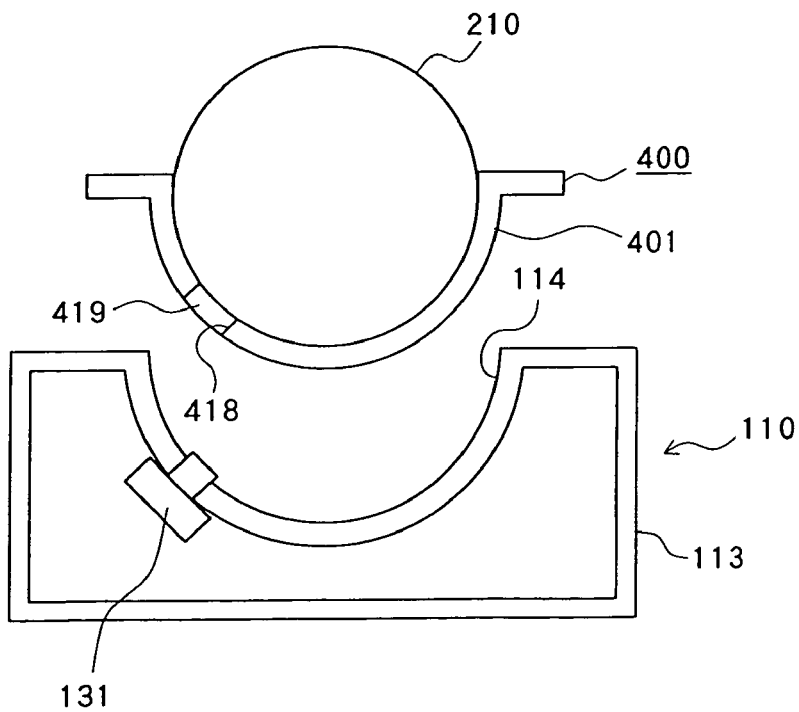

At this point, as shown in FIG. 8b, cylinder member 210 comes into contact with contact-transfer member 419 protruding into concave 402 of cylinder adapter 400, so that contact-transfer member 419 is moved to the position where it is flush with the outer surface of adapter body 401.

Then, liquid syringe 200 is inserted, together with cylinder adapter 400, from above into concave 114 in injection head 110. Movable holders 121 that are in the open position are automatically turned into the closed position. Adapter flange 416 is now retained at its opposite sides by movable holders 121, and retained at its lower side by stationary holder 122.

Figure 9A:
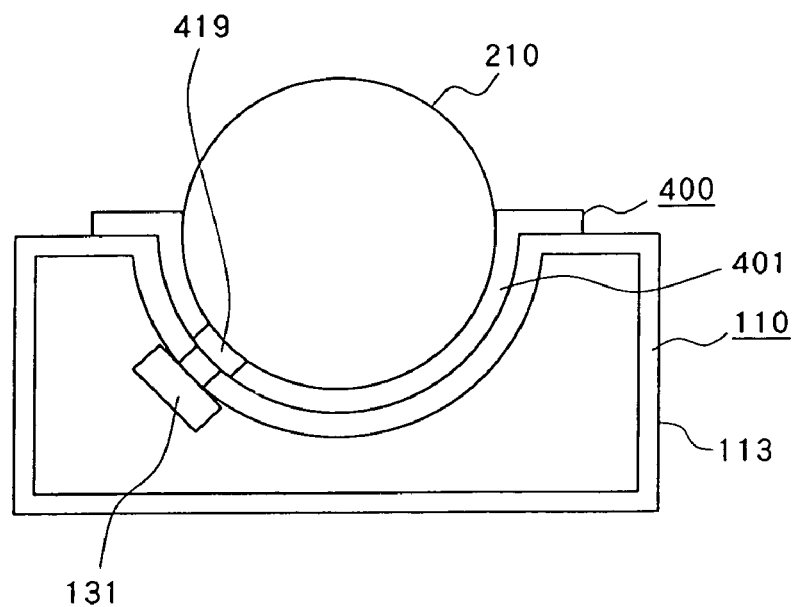
FIGS. 9a and 9b are vertical cross-sectional views showing the manner in which a liquid syringe is mounted on an injection head by a cylinder adapter.

At this point, as shown in FIG. 9a, contact-transfer member 419 of cylinder adapter 400 comes into contact with press switch 131 protruding into concave 112 of injection head 110. Thus, press switch 131 detects the mount of liquid syringe 200 on injection head 110.

Figure 9B:
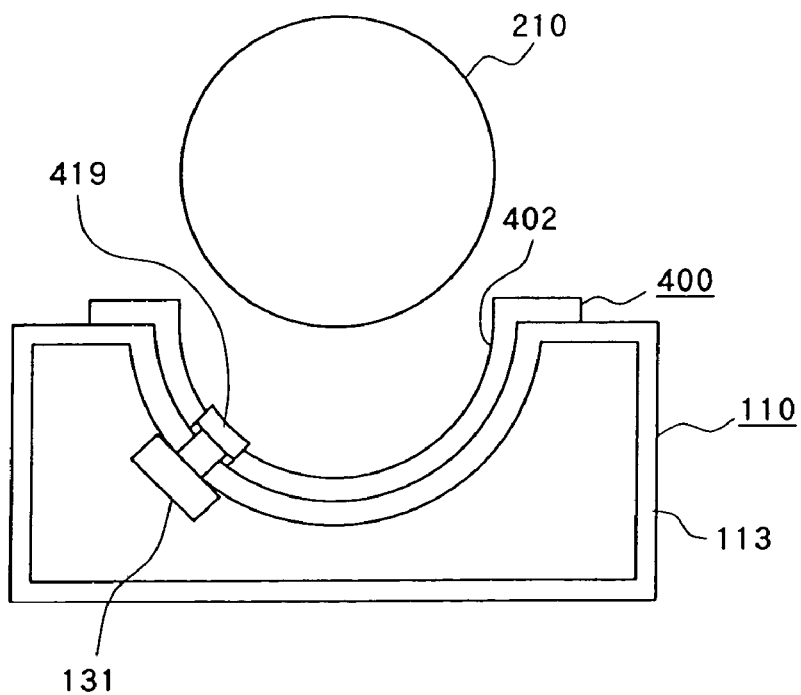

When liquid syringe 200 having the size other than the maximum size is used, it is possible that, as shown in FIG. 9b, cylinder adapter 400 is mounted on injection head 110 and then liquid syringe 200 is mounted on and removed from cylinder adapter 400. In that case, as shown in FIG. 9b, when liquid syringe 200 is removed from cylinder adapter 400 mounted on injection head 100, contact-transfer member 419 of cylinder adapter 400 is moved to the position where it is not detected by press switch 131, so that press switch 131 detects liquid syringe 200 not mounted on injection head 110.

Figure 10:
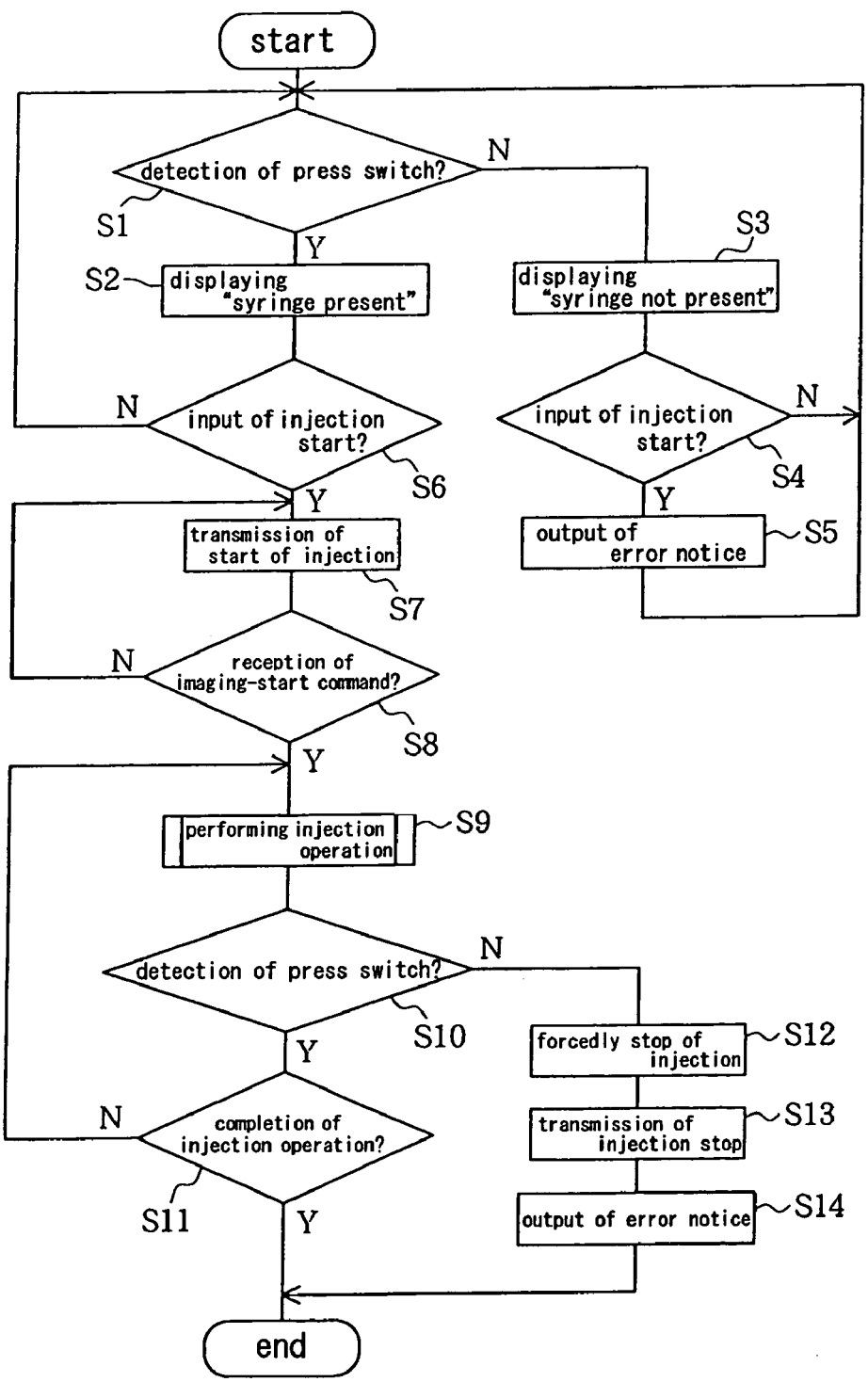
FIG. 10 is a flow chart illustrating the operation of the liquid injector.

Referring to FIG. 10, when press switch 131 detects the mount of liquid syringe 200 on injection head 110 as described above (step S1), microcomputer 130 of liquid injector 100 outputs the display of a guidance message as "Syringe present" on touch panel 104 (step S2).

As shown in FIG. 7a or FIG. 8b or FIG. 9b, when cylinder member 210 of liquid syringe 200 is not mounted in concave 112 of injection head 110, microcomputer 130 outputs the display of a guidance message as "Syringe not present" on touch panel 104 in accordance with the detection result of press switch 131 (steps S1, S3).

While presses switch 131 detects liquid syringe 200 not mounted (steps S1, S3), if the operator makes entry to start the injection with console panel 103 and/or touch panel 104 (step S4), an error guidance as "Check mount of syringe" is output as display on touch panel 104 (step S5).

On the other hand, while press switch 131 detects the mount of liquid syringe 200 on injection head 110 as described above (steps S1, S2), if the operator makes entry to start injection with console panel 103 and/or touch panel 104 (step S6), liquid injector 100 transmits data for starting injection to control unit 302 of MRI apparatus 300 (step S7).

While control unit 302 receives no data for starting injection from liquid injector 100, it disables the operation of imaging unit 301. When it receives data for starting injection, it enables the operation of imaging unit 301. In that state, if the operator makes entry to start imaging, control unit 302 transmits data for starting imaging back to liquid injector 100 and starts imaging by imaging unit 301, for example, after it waits for a predetermined time period which is necessary for a contrast media to reach the affected area.

When liquid injector 100 receives the data for starting imaging from MRI apparatus 300 in response to the transmission of data for starting injection as described above (steps S7, S8), it activates piston actuating mechanism 116 to inject a liquid such as contrast media into the patient from liquid syringe 200 (step S9).

At this point, microcomputer 130 of liquid injector 100 continuously monitors the detection of liquid syringe 200 by press switch 131 (step S10). If the detection by press switch 131 is maintained during the liquid injection, a determination is made as to whether the injection operation is completed (Step S11). If the detection by press switch 131 is lost during the liquid injection, it forced stops piston actuating mechanism 116 (step S12).

Since microcomputer 130 transmits data indicating the injection stop to control unit 302 of MRI apparatus 300 (step S13), control unit 302 also stops forcedly the imaging by imaging unit 301. In addition, an error guidance such as "Syringe not mounted appropriately. Check mount of syringe" is output as display on touch panel 104 (step S14), so that the operator can check the mount of liquid syringe 200 on injection head 110.

Effect of the Embodiment

In liquid injection system 1000 of the embodiment, press switch 131 is placed at the position of liquid injector 100 where it can detect the mount and dismount of liquid syringe 200, so that liquid injector 100 can detect the mount and dismount of liquid syringe 200 by press switch 131.

The operator is notified of the detection result by the display output on tough panel 104, so that the operator can immediately recognize liquid syringe 200 not mounted appropriately, for example. In addition, since microcomputer 130 controls and disables piston actuating mechanism 116 while press switch 131 does not detect liquid syringe 200, it is possible to prevent piston actuating mechanism 116 from being activated while liquid syringe 200 is not mounted appropriately.

Even when press switch 131 detects liquid syringe 200 and piston actuating mechanism 116 is activated, piston actuating mechanism 116 is forcedly stopped if press switch 131 loses the detection of liquid syringe 200. Thus, piston actuating mechanism 116 can be automatically stopped when liquid syringe 200 falls off from the appropriate position, for example.

Furthermore, since liquid injector 100 and MRI apparatus 300 communicate various data with each other to coordinate the various operations, MRI apparatus 300 does not perform imaging operation while press switch 131 of liquid injector 100 does not detect liquid syringe 200, thereby making it possible to prevent useless imaging operation.

Liquid syringe 200 having the maximum size can be directly mounted on liquid injector 100, and liquid syringes 200 having sizes other than the maximum size can be mounted by respective dedicated cylinder adapters 400. In addition, cylinder adapter 400 has contact-transfer member 419 movably supported at the position corresponding to press switch 131, so that press switch 131 can detect mount and dismount of liquid syringe 200 through cylinder adapter 400 as shown in FIG. 9a.

Specifically, as shown in FIG. 8b, even when liquid syringe 200 put on cylinder adapter 400 is mounted on and removed from liquid injector 100, this can be detected by press switch 131. As shown in FIG. 9b, even when liquid syringe 200 is mounted on and removed from liquid injector 100 with cylinder adapter 400 put thereon, this can be detected by press switch 131.

Since contact-transfer member 419 of cylinder adapter 400 is biased to the position where it is not in contact with press switch 131 unless liquid syringe 200 is mounted, press switch 131 can favorably detect mount and dismount of liquid syringe 200 through cylinder adapter 400.

Cylinder adapter 400 holds cylinder flange 213 by the pair of lateral movable holders 411 which can be opened or closed, so that it can appropriately hold cylinder member 210 even when contact-transfer member 419 is biased to protrude into concave 402.

Since injection head 110 holds cylinder flange 213 or adapter flange 416 by the pair of lateral movable holders 121 which can be opened or closed in a similar manner, it can hold appropriately cylinder member 210 or cylinder adapter 400 even when press switch 131 is biased to protrude into concave 114.

When cylinder adapter 400 is not mounted on liquid injector 100, movable holders 411 can be turned. However, when cylinder adapter 400 is mounted on liquid injector 100, movable holders 411 are held in the closed position. Thus, cylinder adapter 400 mounted on liquid injector 100 can reliably fix liquid syringe 200.

When movable holders 411 are held in the closed position, cylinder adapter 400 can be installed in liquid injector 100. However, when movable holders 411 are held in the open position, cylinder adapter 400 cannot be installed in liquid injector 100. Consequently, cylinder adapter 400 can not be installed in liquid injector 100 insofar as liquid syringe 200 is incompletely held by movable holders 411.

When movable holders 411 of cylinder adapter 400 are in the closed position, the lower ends of movable holders 411 are positioned below the axes of holder pivot support mechanisms 414 and the upper ends of movable holders 411 are positioned above the axes of holder pivot support mechanisms 414. Therefore, when liquid cylinder 200 is inserted from above into cylinder adapter 400 with movable holders 411 in the open position, movable holders 411 are automatically turned into the closed position.

When liquid syringe 200 is pulled upwardly from cylinder adapter 400 with movable holders 411 in the closed position, movable holders 411 are automatically turned into the open position. Thus, liquid syringe 200 can easily and intuitively be placed in and removed from cylinder adapter 400. Movable holders 121 of liquid injector 100 and cylinder adapter 400 also operate in the same fashion, so that cylinder adapter 400 can easily and intuitively be mounted on and removed from liquid injector 100.

When cylinder actuating mechanism 116 presses piston member 220 of liquid syringe 200, large stresses are applied to cylinder flange 213 and adapter flange 416. However, since cylinder flange 213 and adapter flange 416 have their lower portions held by stationary holders 412, 122, respectively, cylinder flange 213 and adapter flange 416 are firmly retained in place.

With liquid injection system 1000, liquid injector 100 is used in the vicinity of MRI apparatus 300. Since the drive source of liquid injector 100 comprises an ultrasonic motor made of a nonmagnetic material which does not produce a magnetic field, and the components of cylinder adapter 400 are made of a nonmagnetic material, liquid injector 100 and cylinder adapter 400 can be used in the vicinity of MRI apparatus 300 without any problems.

Modifications of Embodiment

The present invention is not in any way limited to the above-described embodiment, but various changes and modifications may be made therein without departing from the scope of the invention. For example, although it is assumed in the above embodiment that liquid injector 100 is used in the vicinity of MRI apparatus 300, liquid injector 100 may also be used in the vicinity of a CT scanner or an angiography apparatus.

In the above embodiment, liquid syringe 200 having the maximum size is directly mounted on liquid injector 100 and liquid syringes 200 having sizes other than the maximum size are selectively mounted on liquid injector 100 with respective cylinder adapters 400. However, all liquid syringes 200 may be selectively mounted on liquid injector 100 with respective cylinder adapters 400.

In the above embodiment, contact-transfer member 419 of cylinder adapter 400 is biased to the position where it is not in contact with press switch 131. However, it is possible that contact-transfer member 419 is simply movably supported and is moved by biasing of press switch 131.

Figure 11A:
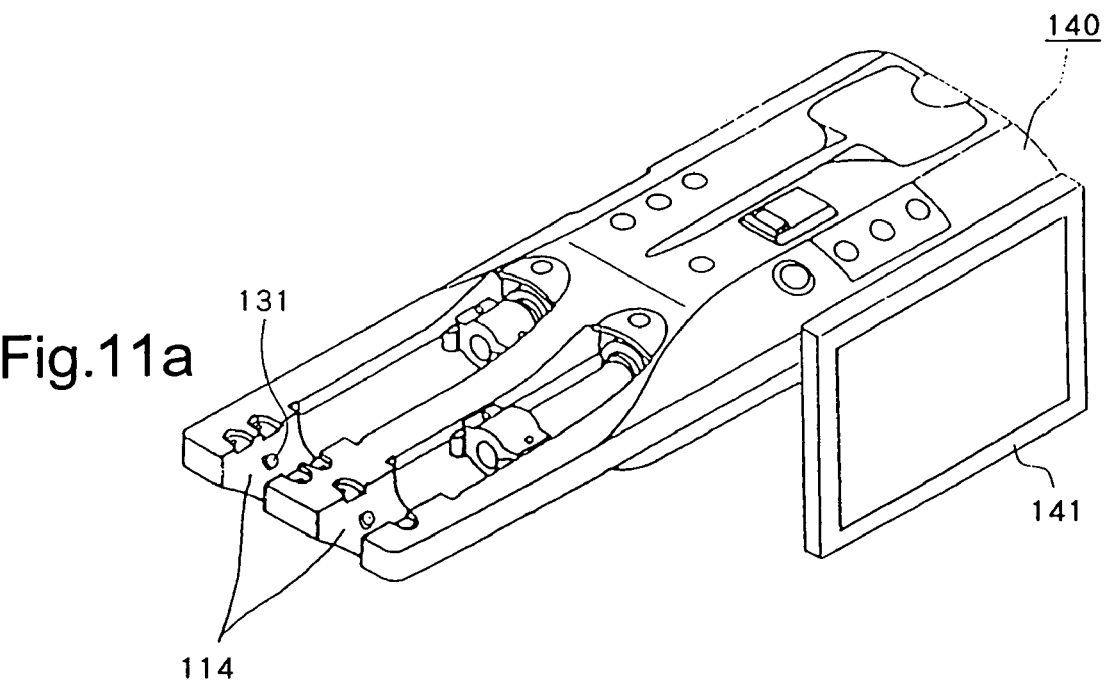
FIG. 11 is a perspective view of an injection head according to a modification.
Figure 11B:
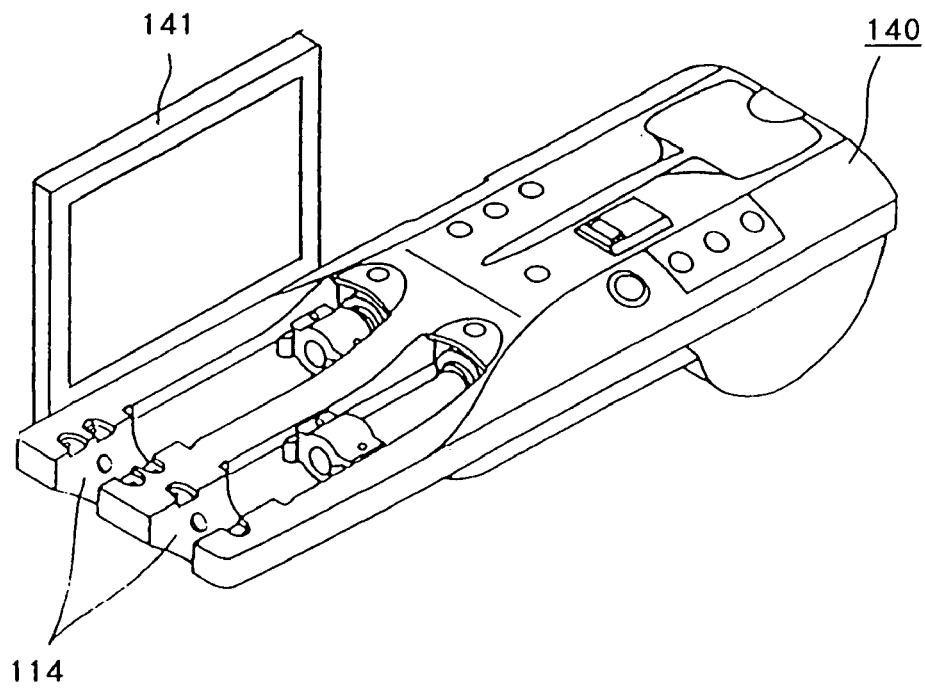

In the above embodiment, one liquid syringe 200 is mounted in one concave 112 of injection head 110 by one cylinder adapter 400. However, as shown in FIGS. 11a and 11b, a plurality of liquid syringes 200 may be mounted on injection head 140 having a plurality of concaves 114.

In the above embodiment, the detection result or the like by press switch 131 is output as display on touch panel 104 separate from injection head 110. However, as shown in FIGS. 11a and 11b, the result or the like may be output as display on display panel 141 provided together with injection head 140. In this case, the detection result, such as whether liquid syringe 200 is appropriately mounted or not, is output as display near the position where liquid syringe 200 is mounted, so that the operator can see the mounting state of liquid syringe 200 more instinctively.

In the above embodiment, cylinder adapter 400 holds piston flange 213 by flange holding mechanism 410 which can be opened or closed, and injection head 110 holds piston flange 213 or adapter flange 416 by flange holding mechanism 120 which can be opened or closed. However, the flange holding mechanism may have any structure as long as it can appropriately hold piston flange 213 or adapter flange 416.

What is claimed is:

1. A liquid injection system comprising a liquid syringe, a liquid injector and a cylinder adapter; the liquid syringe including a cylinder member and a piston member slidably inserted into the cylinder member, and the liquid injector including a cylinder holding mechanism for receiving the cylinder member of the liquid syringe mounted removably thereon and a piston actuating mechanism for relatively moving the piston member with respect to the held cylinder member of the liquid syringe, wherein the liquid injector comprises mount-detecting means, placed at a position to be covered by the cylinder adapter, for detecting contact and separation of the cylinder member when the cylinder member is mounted on and removed from the cylinder holding mechanism, respectively, and wherein the cylinder adapter the allows cylinder holding mechanism to hold the liquid syringe having a size other than the maximum size, and wherein the cylinder adapter comprises an adapter body having an outer surface held by the cylinder holding mechanism and an inner surface holding the cylinder member, and a contact-transfer member supported movably and moved to a position where the contact-transfer member is in contact with the mount-detecting means when the adapter body with the cylinder member mounted thereon is installed in the cylinder holding mechanism.

2. A liquid injection system according to claim 1, wherein the cylinder holding mechanism comprises:

a pair of left and right movable holders, each having an arc-shaped groove defined in an inner surface, to the groove of which a cylinder flange of the liquid syringe with its axis extending forwardly and rearwardly are removably engaged, and a holder pivot support mechanism for pivotally supporting each of the movable holders for vertical angular movement between an open position in which the movable holders are open upwardly for allowing the cylinder flange to be inserted into the grooves and a closed position in which the cylinder flange is retained from left and right sides by the grooves.

3. A liquid injection system according to claim 1, wherein the contact-transfer member is biased to a position where the contact-transfer member is not in contact with the mount-detecting means when the adapter body with the cylinder member not mounted thereon is installed in the cylinder holding mechanism.

4. A liquid injection system according to claim 1, wherein the cylinder adapter includes:

a pair of left and right movable holders, each having an arc-shaped groove defined in an inner surface, to the groove of which the cylinder flange of the liquid syringe with its axis extending forwardly and rearwardly are removably engaged, and a holder pivot support mechanism for pivotally supporting each of the movable holders for vertical angular movement between an open position in which the movable holders are open upwardly for allowing the cylinder flange to be inserted into the grooves and a closed position in which the cylinder flange is retained from left and right sides by the grooves.

5. A liquid injection system according to claim 1, wherein components of the cylinder adapter are made of a nonmagnetic material.

6. A liquid injection system according to claim 1, wherein the liquid injector further includes a display panel for outputting as display the detection result of the mount-detecting means.

7. A liquid injection system according to claim 1, wherein the liquid injector further includes drive control means for controlling the piston actuating mechanism to disable the operation thereof when the mount-detecting means detects no mount of the liquid syringe.

8. A liquid injection system according to claim 1, wherein the liquid injector further comprises:

an imaging diagnostic apparatus for capturing an image of a patient to whom a liquid is injected from the liquid syringe; and control means for controlling the imaging diagnostic apparatus to disable the operation thereof when the mount-detecting means detects no mount of the liquid syringe.

9. A liquid injection system comprising:

a first liquid syringe comprising a cylinder member and a piston member slidably inserted into the cylinder member;

a liquid injector comprising a cylinder holding mechanism for receiving the cylinder member of the liquid syringe mounted removably thereon, and a piston actuating mechanism for moving the piston member relative to the cylinder member when the cylinder member is held by the cylinder holding mechanism;

wherein the liquid injector further comprises a switch that detects contact and separation of the cylinder member when the cylinder member is mounted on and removed from the cylinder holding mechanism, respectively; and a cylinder adapter, wherein the cylinder adapter allows the cylinder holding mechanism to hold the liquid syringe having a size other than the maximum size, and wherein the cylinder adapter comprises an adapter body having an outer surface held by the cylinder holding mechanism and an inner surface holding the cylinder member, and a contact-transfer member supported movably and moved to a position where the contact-transfer member is in contact with the mount-detecting means when the adapter body with the cylinder member mounted thereon is installed in the cylinder holding mechanism.

10. A liquid injection system according to claim 9, wherein the liquid injector further includes a computer for controlling the piston actuating mechanism to disable the operation thereof when the switch detects no mount of a liquid syringe.

11. A liquid injection system according to claim 9, wherein the liquid injector further comprises:

an imaging diagnostic apparatus for capturing an image of a patient into whom a liquid is injected from the liquid syringe; and a computer for controlling the imaging diagnostic apparatus to disable the operation thereof when the switch detects no mount of the liquid syringe.

12. A liquid injection system comprising:

a first liquid syringe comprising a cylinder member and a piston member slidably inserted into the cylinder member;

a second liquid syringe having a smaller size than the first liquid syringe;

a liquid injector comprising a cylinder holding mechanism for receiving the cylinder member of the liquid syringe mounted removably thereon, and a piston actuating mechanism for moving the piston member relative to the cylinder member when the cylinder member is held by the cylinder holding mechanism; and a cylinder adapter for allowing the cylinder holding mechanism to hold the second liquid syringe;

wherein the liquid injector further comprises mount-detecting means for detecting contact and separation of the cylinder member when the cylinder member is mounted on and removed from the cylinder holding mechanism, respectively, wherein the cylinder holding mechanism directly receives the first liquid syringe mounted thereon and receives the second liquid syringe mounted thereon through the cylinder adapter; and the cylinder adapter comprises: an adapter body having an outer surface held by the cylinder holding mechanism and an inner surface holding the cylinder member; and a contact-transfer member that is supported movably and is moved to a Position where the contact-transfer member is in contact with the mount-detecting means when the adapter body with the cylinder member mounted thereon is installed in the cylinder holding mechanism.

13. A liquid injection system according to claim 12, wherein the cylinder adapter further comprises:

a pair of left and right movable holders, each having an arc-shaped groove defined in an inner surface, the grooves of which are removably engaged by the cylinder flange of the liquid syringe; and a holder pivot support mechanism for pivotally supporting each of the movable holders for vertical angular movement between an open position in which the movable holders are open upwardly for allowing the cylinder flange to be inserted into the grooves and a closed position in which the cylinder flange is retained from left and right sides by the grooves.

14. A liquid injection system according to claim 1, wherein the contact-transfer member is movable radially with respect to the syringe.

* * * * *

UNITED STATES PATENT AND TRADEMARK OFFICE
CERTIFICATE OF CORRECTION

PATENT NO. : 7,500,961 B2  Page 1 of 1
APPLICATION NO. : 10/563567
DATED : March 10, 2009
INVENTOR(S) : Shigeru Nemoto It is certified that error appears in the above-identified patent and that said Letters Patent is hereby corrected as shown below:

At column 8, line 36, please delete "forced" and insert therefore, --forcedly--.

Col. 11, line 17; In Claim 1, please delete "the allows" and insert therefore, --allows the--.

Col. 13, line 16; In Claim 12, please delete "Position" and insert therefore, --position--.

Signed and Sealed this

Twenty-ninth Day of September, 2009

David J. Kappos
*Director of the United States Patent and Trademark Office*